US006692452B2

United States Patent
Chow

(10) Patent No.: US 6,692,452 B2
(45) Date of Patent: Feb. 17, 2004

(54) FINGER SPLINT FOR TREATING MALLET FINGER CONDITION

(76) Inventor: James C. Y. Chow, 4121 Veterans Memorial Dr., Mount Vernon, IL (US) 62864

( * ) Notice: Subject to any disclaimer, the term of this patent is extended or adjusted under 35 U.S.C. 154(b) by 188 days.

(21) Appl. No.: 10/043,579

(22) Filed: Jan. 11, 2002

(65) Prior Publication Data

US 2003/0135143 A1 Jul. 17, 2003

(51) Int. Cl.[7] .................................................. A61F 5/00
(52) U.S. Cl. ............................. 602/5; 602/20; 602/22
(58) Field of Search ............................. 602/5, 20, 21, 602/22; 128/846, 869, 882, 880; 2/161.1, 159, 160

(56) References Cited

U.S. PATENT DOCUMENTS

| | | | | |
|---|---|---|---|---|
| 2,209,860 A | * | 7/1940 | Tiedemann | 128/880 |
| 5,230,699 A | * | 7/1993 | Grasinger | 602/22 |
| 5,346,462 A | * | 9/1994 | Barber | 602/30 |
| 5,353,812 A | | 10/1994 | Chow | |
| 5,480,408 A | | 1/1996 | Chow | |
| 5,628,069 A | * | 5/1997 | Ebert | 2/161.1 |
| 5,730,154 A | * | 3/1998 | DeRidder | 128/880 |
| 5,782,850 A | | 7/1998 | Ro | |
| 5,957,944 A | | 9/1999 | Khuri et al. | |

* cited by examiner

Primary Examiner—Michael A. Brown
(74) Attorney, Agent, or Firm—Polster, Lieder Woodruff & Lucchesi L.C.

(57) ABSTRACT

A splint (10) worn by sufferers of mallet finger. The splint comprises a sleeve (12) sized to readily fit over the end of a finger (F) having a damaged tendon causing the mallet finger. The sleeve extends at least as far as the DIP joint of the finger. A pocket (14) is formed in the sleeve and a curved rigid plate (16) having an elbow (18) formed intermediate its ends is positioned along the underside of the finger. A padding material (20) fits between the plate and the finger to cushion the finger. The curvature of the plate holds the outer end of the finger in a hyperextended position with the DIP joint immobilized so to promote healing of the finger.

17 Claims, 1 Drawing Sheet

FINGER SPLINT FOR TREATING MALLET FINGER CONDITION

CROSS REFERENCE TO RELATED APPLICATIONS

None

STATEMENT REGARDING FEDERALLY SPONSORED RESEARCH OR DEVELOPMENT

Not applicable

BACKGROUND OF THE INVENTION

This invention relates to orthopedic devices; and more particularly, to a mallet finger splint for use by those suffering from an injury to their distal interphalangeal (DIP) finger joint.

When the tip end of a finger strikes, or is struck by an object, the end of the finger is bent. If the force on the finger is sufficiently great, it can be pushed beyond its normal limits which is typically 35° to 40° toward the palm of the hand. Past this limit, the finger can suffer damage (tearing) to the tendon controlling the muscles which move the finger. Sufficient force will cause the tendon to detach, so that the tip end of the finger cannot be straightened, but rather hangs down abnormally. A common activity in which this injury occurs is baseball, because of which this condition is sometimes referred to as "baseball" finger. In playing the sport, it is not uncommon for a ball to strike the tip in end of the finger and bend it into an awkward position, causing the injury.

Mallet finger is a painful injury. Sometimes, when the tendon is torn, pieces of bone are pulled away from the bone as well. Sometimes, if finger joints are jammed together, cartilage damage results. Once the injury occurs, the finger must be immobilized for at least several weeks. Otherwise, a chronic injury results. Sometimes surgery is the only effective way to correct the problem.

Treatment of mallet finger often involves placing a splint on the finger. The splint is fitted onto the end of the finger to both immobilize the distal interphalangeal (DIP) joint of the finger and to hold the end of the finger in a slight hyperextension. It is not uncommon for the splint to be continuously worn for up to 6–8 weeks and then be worn only at night for another 3–6 week period. After this latter period, the injured person is given a series of mobilization exercises to perform to help regain a range of motion with the finger.

There are a number splints used in the treatment of mallet finger. Some are used in order to avoid splint related skin problems. Others require percutaneous pinning of the DIP joint to secure the splint in place. Many of the splints currently in use are not easy to wear, and some do not always provide the immobilization necessary to promote healing. What is described herein is a simple, easy to use mallet finger splint which is readily attached to the person's finger, can be worn for extended periods of time without causing discomfort to the wearer and can readily easily removed for therapy sessions, cleaning, and the like.

BRIEF SUMMARY OF THE INVENTION

Among the several objects of the present invention may be noted a splint worn by sufferers of mallet finger. The splint comprises a tube sized to readily fit over the end of a finger having a damaged tendon causing the mallet finger. A pocket formed along one portion of the tube receives a curved, rigid plate which is positioned on the underside of the finger. A padding material fits between the plate and the finger to cushion the finger. The curvature of the plate holds the outer end of the finger in a hyperextended position with the DIP joint immobilized. Other objects and features will be in part apparent and in part pointed out hereinafter.

BRIEF DESCRIPTION OF THE SEVERAL VIEWS OF THE DRAWINGS

The objects of the invention are achieved as set forth in the illustrative embodiments shown in the drawings which form a part of the specification.

Corresponding reference characters indicate corresponding parts throughout the several views of the drawings.

DETAILED DESCRIPTION OF INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. As various changes could be made in the above constructions without departing from the scope of the invention, it is intended that all matter contained in the above description or shown in the accompanying drawings shall be interpreted as illustrative and not in a limiting sense.

Figure 1:
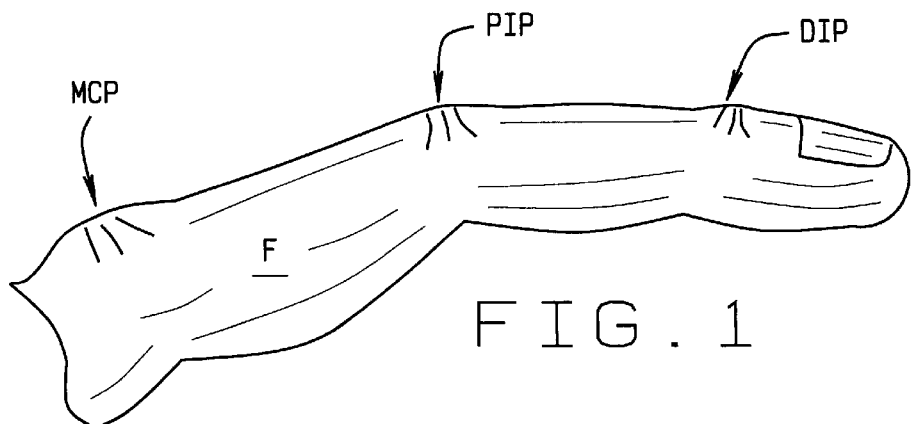
FIG. 1 is a simplified view of a person's hand.

Referring to the drawings, FIG. 1 is a simplified representation of a finger F. The outer joint of the finger is referred to as the distal interphalangeal (DIP) joint, the intermediate joint as the proximal interphalangeal (PIP) joint, and the inner joint or knuckle as the metacarpophalangeal (MCP) joint. As discussed above, a mallet finger injury effects the DIP joint.

Figure 2:
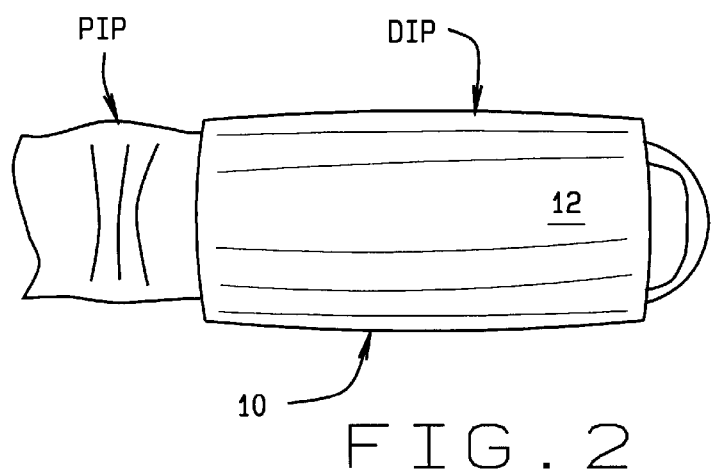
FIG. 2 illustrates the mallet splint worn on a person's finger.
Figure 3:
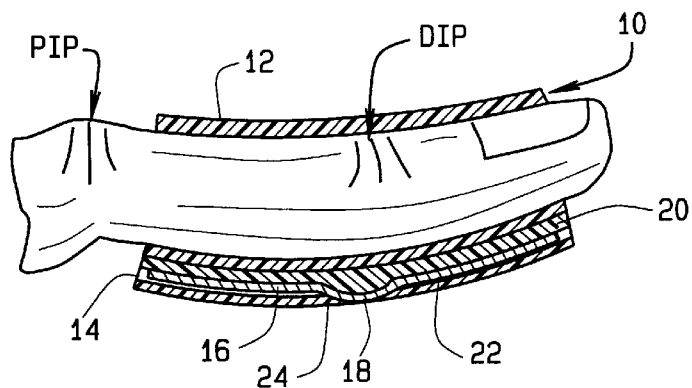
FIG. 3 is a sectional view of the splint as worn.

A finger splint 10, as shown in FIG. 2, is for use in the treatment of mallet finger. Splint 10 first includes a hollow, tubular sleeve 12 sized to fit over the end of the finger. The sleeve is open at each end and the length of the sleeve is such that when worn it extends past the DIP joint of the finger. However, as shown in FIGS. 2 and 3, the sleeve does not extend so far as the PIP joint of the finger. Thus, as described below, when the splint is worn, the DIP joint is immobilized, but the PIP joint is not. This allows the finger to be movable even though the outer end of the finger cannot flex. Immobilizing the finger in this manner helps treat the mallet finger condition while still allowing the hand to be used.

Sleeve 10 is made from lightweight, elasticized material. This makes the sleeve easy to put on and take off, as well as comfortable to wear. Further, by being open at each end, one size splint can be used by people whose fingers are of different lengths since the sleeve can be readily moved along the finger to properly position it.

Figure 4:
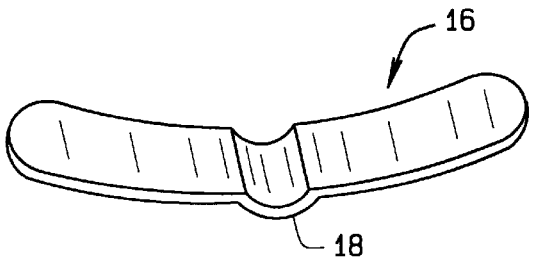
FIG. 4 is a perspective view of the splint.

A pocket 14 is formed in sleeve 12, on the underside of the sleeve as shown in FIG. 3, and extends generally the length of the sleeve. A curved, rigid plate 16 fits in this pocket. The plate is preferably made of a lightweight, yet stiff metal, or of a stiff plastic. Referring to FIG. 4, plate 16 is shown to have a shallow, concave curvature extending from one end of the plate to the other. A recess or elbow 18 is formed intermediate the length of the plate, approximately halfway along the length of the plate, and extends across the plate. The elbow reinforces the plate to help it hold the outer end of the finger in a hyperextended position, when the splint is being worn, with the DIP joint immobilized. Since sleeve 12 is open at both ends, it is adjustable on the wearer's finger. This allows the wearer to readily position the splint so elbow 18 is directly beneath the DIP joint as shown in FIG. 3. A further advantage of this is that the same size splint can be worn by a number of people whose hands and fingers are of different sizes. Those skilled in the art will understand that plate 16 is a replaceable item and a number of plates of different rigidities can be used in the splint. This allows the splint to be better accommodated to the wearer some of whom may require a stiffer splint than others.

A padding material 20 fits between plate 16 and the finger to cushion the finger and make the splint more comfortable to wear. The material is provided as a thin sheet 22 which preferably fits in pocket 14 together with plate 16. The underside of sheet 22 includes a projection 24 shaped to fill the area formed by elbow 18 of the plate. This padding material helps stiffen the plate.

In use, the splint is fitted over the end of the finger until the inner end of the sleeve extends past the DIP joint. The sleeve is then adjusted until elbow 18 of plate 16 is positioned underneath the joint. The curvature of the plate now forces the outer end of the finger to hyperextended. At the same time, the plate prevents movement of the DIP joint. However, the PIP joint is movable so the finger can be used to some extent. When the splint is removed, the plate and padding can be removed from the pocket for cleaning. At the same time, the sleeve can be machine washed to clean it.

In view of the above, it will be seen that the several objects and advantages of the present invention have been achieved and other advantageous results have been obtained.

Having thus described the invention, what is claimed and desired to be secured by Letters Patent is:

1. A finger splint for use in the treatment of mallet finger comprising:
    a sleeve sized to fit over the end of a finger and extending to at least the distal interphalangeal (DIP) joint of the finger;
    a pocket formed in the sleeve and extending generally the length of the sleeve;
    a curved, rigid plate fitting in the pocket for holding the outer end of the finger in a desired position with the DIP joint immobilized, the plate having a recess formed intermediate its length to reinforce the splint in immobilizing the DIP joint thereby to promote healing of the finger.

2. The finger splint of claim 1 for holding the outer end of the finger in a hyperextended position.

3. The finger splint of claim 1 in which the sleeve comprises a hollow tube open at both ends to facilitate inserting the sleeve onto, and removing it from, the end of the finger.

4. The finger splint of claim 3 further including a padding material fitted between the plate and the finger to cushion the finger.

5. The finger splint of claim 3 wherein the recess in the plate extends transversely of the plate and is positioned beneath the DIP joint when the splint is being worn.

6. The finger splint of claim 5 in which padding material is received in the recess to further stiffen the plate.

7. A finger splint for use in the treatment of mallet finger comprising:
    a hollow, tubular sleeve sized to fit over the end of a finger and extending past the distal interphalangeal (DIP) joint of the finger when placed on the finger;
    a pocket formed in the sleeve and extending generally the length of the sleeve;
    a curved, rigid plate received in the pocket for holding the DIP joint of the finger immobilized and the outer end of the finger in a hyperextended position, the plate having a recess formed intermediate its length to reinforce the splint in immobilizing the DIP joint thereby to promote healing of the finger.

8. The finger splint of claim 7 in which the length of the sleeve is such that it extends past the DIP joint but does not extend so far as the proximal interphalangeal (PIP) joint of the finger so that the DIP joint is immobilized when the splint is worn, but the PIP joint is not.

9. The finger splint of claim 8 in which the recess in the plate comprises an elbow extending transversely of the plate and located beneath the DIP joint when the splint is in place.

10. The finger splint of claim 9 further including a padding material fitted between the plate and the finger to cushion the finger.

11. The finger splint of claim 10 in which padding material is received in the recess of the plate to further stiffen the plate.

12. The finger splint of claim 9 in which the plate is a metal plate.

13. The finger splint of claim 9 in which the plate is of a rigid, plastic material.

14. The finger splint of claim 7 in which the sleeve is made of a lightweight, elasticized material so to be easy to put on and take off, and comfortable to wear.

15. The finger splint of claim 14 in which the sleeve is open at each end so to be adjustable to a person's finger when worn.

16. The finger splint of claim 7 in which the plate has a shallow, concave curvature from one end to the other.

17. The finger splint of claim 16 in which the recess is formed approximately halfway along the length of the plate.

* * * * *